(12) United States Patent
Beaudet et al.

(10) Patent No.: US 8,088,605 B2
(45) Date of Patent: Jan. 3, 2012

(54) EXOPOLYSACCHARIDES DELIVERY SYSTEM FOR ACTIVE MOLECULES

(75) Inventors: Nicolas Beaudet, Bury (CA); Claude Dupont, Blainville (CA); Pierre Lemieux, Ste-Thérèse (CA); Eric Simard, Laval (CA); Philippe Goyette, Montreal (CA)

(73) Assignees: Technologies Biolactics Inc., Laval (CA); INRS (Institute National de Recherche Scientifique), Quebec (CA)

( * ) Notice: Subject to any disclaimer, the term of this patent is extended or adjusted under 35 U.S.C. 154(b) by 1547 days.

(21) Appl. No.: 10/537,118

(22) PCT Filed: Dec. 4, 2003

(86) PCT No.: PCT/CA03/01899
§ 371 (c)(1),
(2), (4) Date: Feb. 9, 2006

(87) PCT Pub. No.: WO2004/050057
PCT Pub. Date: Jun. 17, 2004

(65) Prior Publication Data
US 2006/0154893 A1 Jul. 13, 2006

Related U.S. Application Data

(60) Provisional application No. 60/430,690, filed on Dec. 4, 2002.

(51) Int. Cl.
*C12P 19/04* (2006.01)
*A61K 31/715* (2006.01)

(52) U.S. Cl. .......................................... 435/101; 514/54

(58) Field of Classification Search ........................ None
See application file for complete search history.

(56) References Cited

U.S. PATENT DOCUMENTS

| | | | |
|---|---|---|---|
| 4,578,458 A | 3/1986 | Pier | |
| 6,140,312 A | 10/2000 | Falk et al. | |
| 6,350,458 B1 | 2/2002 | Modi | |
| 7,083,787 B2 * | 8/2006 | Duke et al. | 424/184.1 |
| 2002/0090392 A1 * | 7/2002 | Campbell et al. | 424/450 |
| 2002/0131995 A1 | 9/2002 | Szoka | |
| 2006/0057131 A1 * | 3/2006 | Simard et al. | 424/93.45 |

FOREIGN PATENT DOCUMENTS

| | | | |
|---|---|---|---|
| FR | 2 631 829 A | | 12/1989 |
| WO | WO-99/02151 A | | 1/1999 |
| WO | WO/00/37051 | * | 6/2000 |
| WO | WO/00/41730 | * | 7/2000 |
| WO | WO-00/41730 A | | 7/2000 |
| WO | WO-03/053158 A | | 7/2003 |

OTHER PUBLICATIONS

Kachlany et al., Structure and carbohydrate analysis of the exopolysaccharide capsule of *Pseudomonas putida* G7, Environmental Microbiology 2001, vol. 3 (12), pp. 774-784.*
Biology Online Dictionary "hyaluronic acid"; also available at http://www.biology-online.org/bodict/index.php?title=Hyaluronic_acid &printable=yes; last viewed Sep. 9, 2009.*
Chong, Barrie F. et al., Appl Microbiol Biotechnol, Microbial hyaluronic acid production, vol. 66, pp. 341-351 (2005).*
Abraham, Analia G. et al., Journal of Dairy Research "Characterization of kefir grains grown in cows' milk and in soya milk", vol. 66, pp. 327-333 (1999).*
Maeda, Hiroaki et al., Journal of Agricultural and Food Chemistry "Structural Characterization and Biological Activities of an Exopolysaccharide Kefiran Produced by *Lactobacillus kefiranofaciens* WT-2B", vol. 52, pp. 5533-5538 (2004).*
Micheli, L. et al., Appl. Microbiol. Biotechnol. "Isolation and characterisation of a ropy *Lactobacillus* strain producing the exopolysaccharide kefiran", vol. 53, pp. 69-74 (1999).*
Jolly, L. et al., Antonie van Leeuwenhoek "Exploiting exopolysaccharides from lactic acid bacteria", vol. 82, pp. 367-374 (2002).*
Yang, Zhennai, Academic Dissertation, "Antimicrobial Compounds and Extracellular Polysaccharides Produced by Lactic Acid Bacteria: Structures and Properties", Department of Food Technology, University of Helsinki, Mar. 2000.*
Online! XP002280832, URL:<http://www.roempp.com/thieme-chemistry/roempp/prod/index1.html>, retrieved from the Internet on May 14, 2004.
Burnham, American Journal of Hospital Pharmacy, American Society of Hospital Pharmacists, Bethesda, MD, US, vol. 51, No. 2, Jan. 15, 1994, pp. 210-218.
Amorena et al., Vaccine, 1994, vol. 12, No. 3, pp. 243-249.
Na et al., Pharmaceutical Research, New York, vol. 19, No. 5, May 2002, pp. 681-688.

* cited by examiner

*Primary Examiner* — Shaojia Anna Jiang
*Assistant Examiner* — Bahar Schmidtmann
(74) *Attorney, Agent, or Firm* — Birch, Stewart, Kolasch & Birch, LLP

(57) ABSTRACT

The present invention relates to a delivery system for delivery of an active molecule to a patient, the delivery system comprising a population of exopolysaccharide micelles, each micelle defining a core for containing the active molecule.

32 Claims, 2 Drawing Sheets

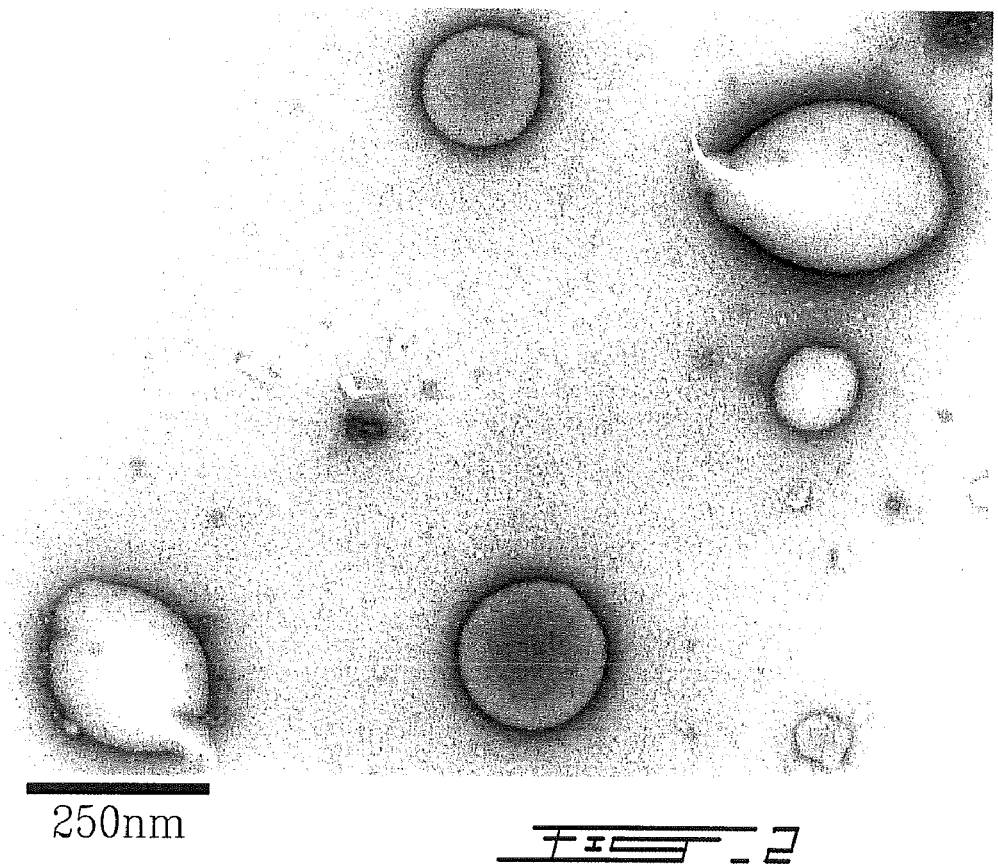
250nm
FIG. 2
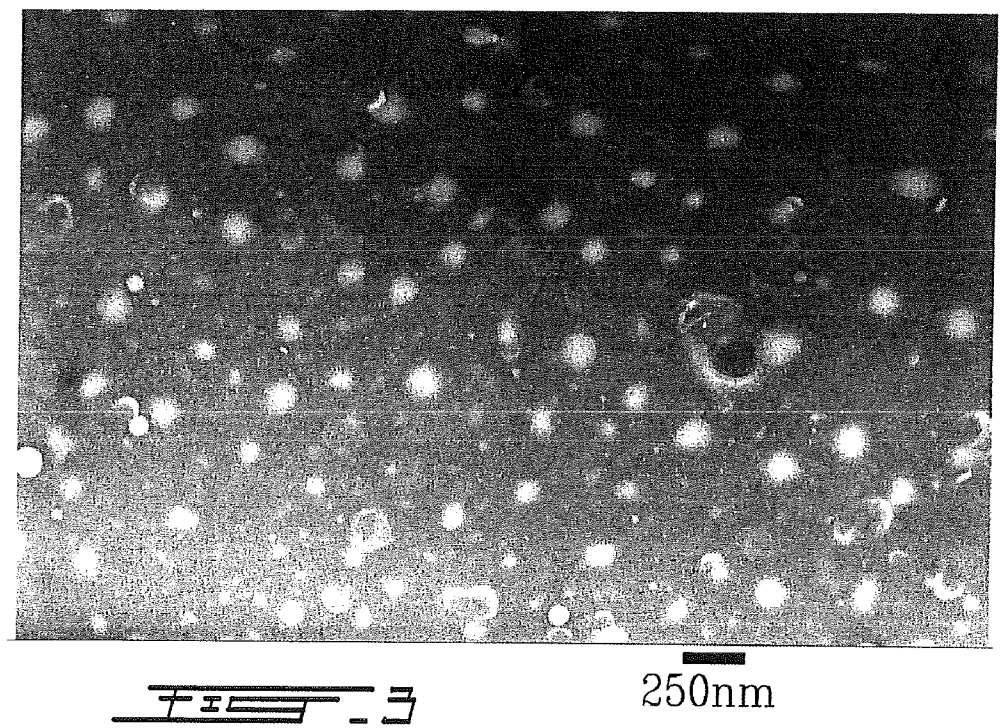
FIG. 3   250nm

EXOPOLYSACCHARIDES DELIVERY SYSTEM FOR ACTIVE MOLECULES

BACKGROUND OF THE INVENTION (a) Field of the Invention

This invention relates to exopolysaccharide delivery system of active molecules into a patient and/or increase the activity of the active molecules.

(b) Description of Prior Art

Encapsulation of bioactive compounds in natural or synthetic matrices has been extensively studied over the past decades. Advantages of encapsulation are numerous. Firstly, it provides protection from the inactivation or degradation of the bioactive compound. Secondly, it controls the kinetics of compound release, allowing the optimization of the blood concentration profile. Thirdly, it can also improve therapeutic indices of bioactive compounds like that described with micellar systems. This optimization diminishes the deleterious effects of bioactive compounds with short half lives. In addition, it permits a reduction in toxicity or synergize with the formulated drugs leading to a better treatment for the patient.

Many systems have been described to improve formulation of bioactive compounds. Among them are found colloidal drug delivery systems that are promising such as liposomes, microspheres, nanospheres and block copolymer micelles that increase the therapeutic index and improve the selectivity of various potent drugs (Gregoriadis G., (1995) TIBS, 13:527-537; Muller R. H., (1991) Colloidal Carriers for Controlled Drug Delivery and Targeting: Modification, Characterization and In vivo Distribution, CRC Press Inc., Florida; Kabanov A. V., Alakhov V. Y. (1997). "Micelles of Amphiphilic Block Copolymers as Vehicles for Drug Delivery" In Amphiphilic Block Copolymers: Self-Assembly and Applications edited by Alexamdris P., Lindman B., Elsevier, Netherlands; Kwon G. et al. (1997) J. Controlled Release, 48:195-201; La S. B. et al. (1996) Journal of Pharmaceutical Sciences, 85:85-90; Kataoka K. et al. (1992) J. Control. Release, 24:119-132). These vehicles optimize the therapeutic efficacy of drugs by preventing their rapid elimination from the body, reducing their systemic toxicity, delaying their degradation and optimizing their metabolism (Muller R. H. (1991) supra; Kabanov A. V., Alakhov V. Y. (1997) supra). In addition, they also provide for effective delivery of drugs to specific target sites (Muller R. H., (1991) supra) and aid in overcoming both transport limitations and defense mechanisms associated with the multi-drug resistance phenotype.

Various approaches have been developed to provide continuous delivery of various biologically active agents, and, although these have overcome some of the problems of delivering the agents, numerous problems remain such as the linearity of release, bioavailability, absorption, biocompatibility of the materials used and loading capacity.

It would be highly desirable to be provided with a natural biopolymers forming micelles, being easily and inexpensively produced, that are enabling the delivery of an active molecule to a patient.

SUMMARY OF THE INVENTION

One aim of the invention is to use exopolysaccharides (EPS) micelles as a drug delivery system.

Another aim of the present invention is to describe a method of production of exopolysaccharides having micellar properties.

The active molecule may be lipophilic, hydrophilic, hydrophobic.

The micellar system of the present invention is also suitable to the cosmetic industry such as in the delivery of active agents in creams, toiletries, deodorants, skin and sunscreen preparation. The micellar system of the present invention is also useful in perfumes, by stabilizing the unstable components thereof and by controlling the release kinetics of the fragrance upon application.

In accordance with the present invention there is provided a delivery system for delivery of an active molecule to a patient, the delivery system comprising a population of exopolysaccharide micelles, each micelle defining a core for containing the active molecule.

In a preferred embodiment of the present invention, the exopolysaccharide is produced by lactic acid bacteria, more preferably the bacteria is selected from the group consisting of *Lactobacillus* strain R2C2, *Lactobacillus* strain Inix, *Lactobacillus* strain Es1, *Lactobacillus* strain K2. Alternatively, the exopolysaccharide can be produced by a yeast like, but not limited to *Candida kefyr* or *Candida norvegensis*.

In accordance with a preferred embodiment of the present invention, the active molecule is selected from the group consisting of DNA, RNA, protein, peptide, peptidomimetic, virus, bacteria, neutraceutical product and pharmaceutical agent. Preferably, the pharmaceutical agent is selected from the group consisting of analgesic, anesthetic, antibiotic, anti-cancer, anti-inflammatory, and antiviral.

The anticancer agent is preferably selected from the group consisting of alkylating agents, alkyl sulfonates, aziridines, ethylenimines, methylamelamines, acetogenins, camptothecin, bryostatin, callystatin, CC-1065, cryptophycins, dolastatin; duocarmycin, eleutherobin, pancratistatin, sarcodictyin, spongistatin, nitrogen mustards, nitrosureas, antibiotics, anti-metabolites, folic acid analogues such as denopterin, methotrexate, pteropterin, trimetrexate, purine analogs, pyrimidine analogs, androgens, anti-adrenals, folic acid replenisher, aceglatone, aldophosphamide glycoside, aminolevulinic acid, amsacrine, bestrabucil, bisantrene, edatraxate, defofamine, demecolcine, diaziquone, elformithine, elliptinium acetate, epothilone, etoglucid, gallium nitrate, hydroxyurea, lentinan, lonidamine, maytansinoids, mitoguazone, mitoxantrone, mopidamol, nitracrine, pentostatin, phenamet, pirarubicin, podophyllinic acid, 2-ethylhydrazide, procarbazine, PSK®, razoxane, rhizoxin, sizofiran, spirogermanium, tenuazonic acid, triaziquone, 2,2',2"-trichlorotriethylamine, trichothecenes, urethan, vindesine, dacarbazine, mannomustine, mitobronitol, mitolactol, pipobroman, gacytosine, arabinoside, thiotepa, taxanes, chlorambucil, gemcitabine, 6-thioguanine, mercaptopurine, methotrexate, platinum, vinblastine, platinum, etoposide, ifosfamide, mitomycin C, mitoxantrone, vincristine, vinorelbine, navelbin, novantrone, teniposide, daunomycin, aminopterin, xeloda, ibandronate, CPT-11, topoisomerase inhibitor RFS 2000, difluoromethylornithine, retinoic acid, capecitabine, bisphosphonates and anti-hormonal agents that act to regulate or inhibiting hormone action in hormonal dependent cancers.

The anti-hormonal agent is preferably an anti-estrogens or an anti-androgens selected from the group consisting of flutamide, nilutamide, bicalutamide, leuprolide, and goserelin, and pharmaceutically acceptable salts, acids or derivatives thereof.

The alkylating agents are preferably selected from the group consisting of thiotepa and cyclosphosphamide (CYTOXAN™).

The alkyl sulfonates are preferably selected from the group consisting of busulfan, improsulfan and piposulfan.

The aziridines are preferably selected from the group consisting of benzodopa, carboquone, meturedopa, and uredopa.

The methylamelamines are preferably selected from the group consisting of altretamine, triethylenemelamine, trietylenephosphoramide, triethylenethiophosphaor-amide and trimethylolomelamine.

The acetogenins are preferably selected from the group consisting of bullatacin and bullatacinone.

The camptothecin is preferably the synthetic analogue topotecan.

The CC-1065 is preferably selected from the group consisting of adozelesin, carzelesin and bizelesin synthetic analogues thereof.

The cryptophycins are preferably selected from the group consisting of cryptophycin 1 and cryptophycin 8.

The duocarmycin is preferably selected from the group consisting of KW-2189 and CBI-TMI.

The nitrogen mustards are preferably selected from the group consisting of chlorambucil, chlornaphazine, cholophosphamide, estramustine, ifosfamide, mechlorethamine, mechlorethamine oxide hydrochloride, melphalan, novembichin, phenesterine, prednimustine, trofosfamide and uracil mustard.

The nitrosureas are preferably selected from the group consisting of carmustine, chlorozotocin, fotemustine, lomustine, nimustine, ranimustine.

The anti-metabolites are preferably selected from methotrexate and 5-fluorouracil (5-FU).

The purine analogs are preferably selected from the group consisting of fludarabine, 6-mercaptopurine, thiamiprine and thioguanine.

The pyrimidine analogs are preferably selected from the group consisting of ancitabine, azacitidine, 6-azauridine, carmofur, cytarabine, dideoxyuridine, doxifluridine, enocitabine and floxuridine.

The androgens are preferably selected from the group consisting of calusterone, dromostanolone propionate, epitiostanol, mepitiostane, testolactone.

The anti-adrenals are preferably selected from the group consisting of aminoglutethimide, mitotane and trilostane.

The antibiotics are preferably selected from the group consisting of enediyne antibiotics, aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin.

The enediyne antibiotics are preferably selected from the group consisting of calicheamicin more preferably calicheamicin γ1l and calicheamicin θ1l, dynemicin more preferably dynemicin A, esperamicin, neocarzinostatin chromophore and related chromoprotein enediyne antibiotic chromophores.

In accordance with a preferred embodiment of the present invention, the micelles have a diameter varying from about 50 nanometers to about 700 nanometers.

In accordance with the present invention, there is provided a pharmaceutical composition comprising the delivery system of the present invention in association with a pharmaceutically acceptable carrier and method of use thereof.

In accordance with the present invention, there is provided an immunomodulator composition comprising an immunomodulating amount of the delivery system of the present invention in association with a pharmaceutically acceptable carrier and method of use thereof.

In accordance with the present invention, there is provided a method for producing the delivery system of the present invention, comprising the step of incubating exopolysaccharide in a suitable medium for a time sufficient to form micelle.

Administration of the delivery vehicle of the present invention can be performed by a route selected from the group consisting out local, parenteral, peritoneal, mucosal, dermal, epidermal, subcutaneous, transdermal, intramuscular, nasal, oral, topical, vaginal, rectal, intra-ocular, intravenous, intra-arterial and by inhalation.

For the purpose of the present invention the following terms are defined below.

The term "active molecule" is intended to mean, without limitations, nonpolar, lipophilic drugs, vitamins, polar molecules, immunosuppressants, immunoactive agents, nutraceuticals, peptidomimetics mimicking growth factors and their antagonists and immunomodulator agents All references herein are hereby incorporated by reference.

BRIEF DESCRIPTION OF THE DRAWINGS

FIG. 2 is an electronic microscopy image of pure EPS micelles; and

FIG. 3 is an electronic microscopy image of EPS micelles having 1% critical micellar concentration.

DETAILED DESCRIPTION OF THE INVENTION

Figure 1:
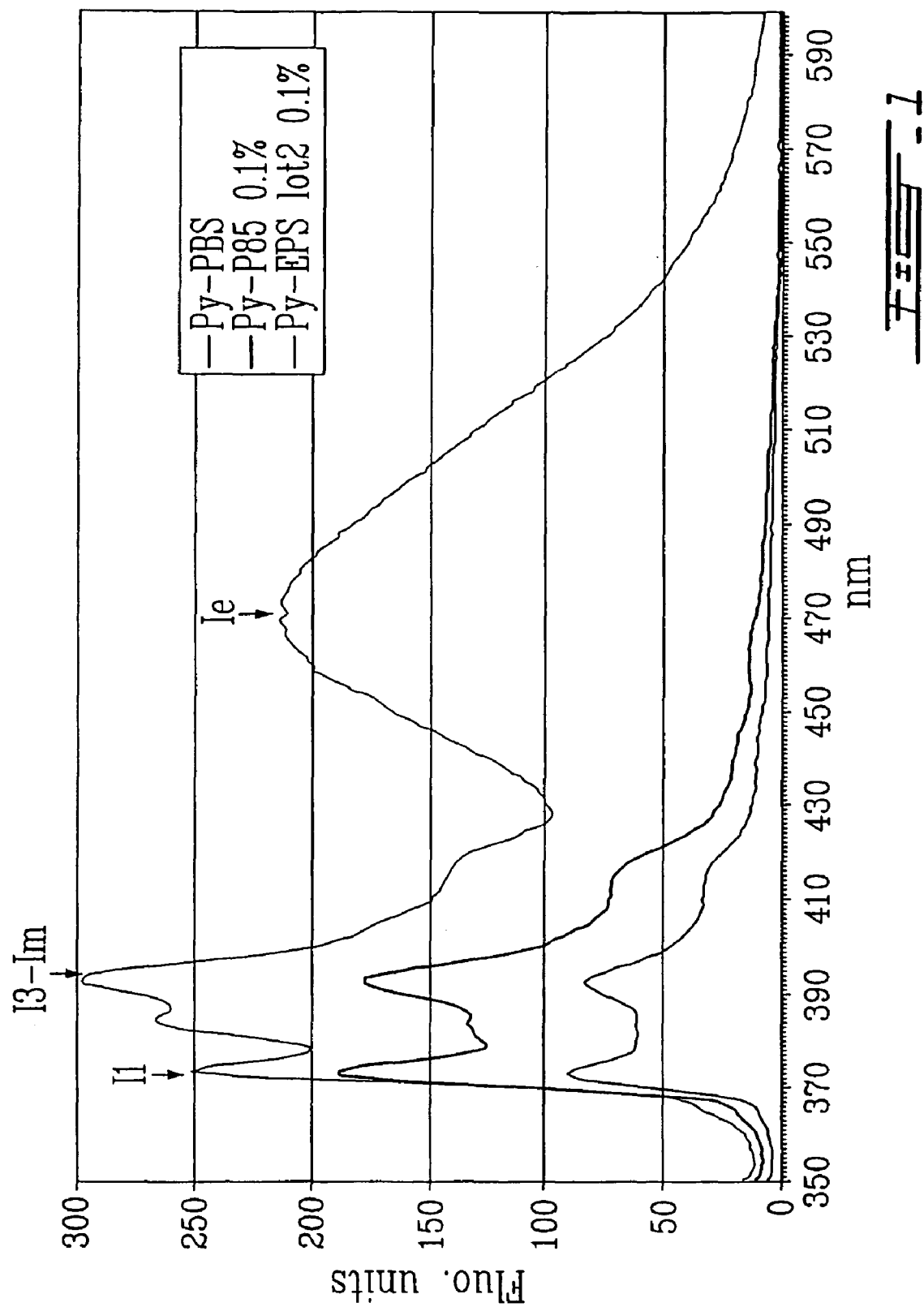
FIG. 1 illustrates scans of pyrene dissolved in PBS, P85 and EPS.

In accordance with the present invention, there is provided a delivery system comprising exopolysaccharide micelles for delivering an active molecule to a patient.

Exopolysaccharides (EPS) produced by lactic acid bacteria (LAB) are known to act as viscosifying agents in fermented foods (Yang, Z. (2000) Antimicrobial and extracellular polysaccharides produced by lactic acid bacteria: Structures and properties, PhD thesis, University of Helsinki, Helsinki, 61 pp.) and as cytokine inducers in vitro (Chabot, S. et al, (2001) Lait, 81:683-697). The rheological and immunomodulator properties of EPS are based on their monomeric composition and their assembling, conferring to those molecules a neutral to charged tri-dimensional structure that can actively interact with its environment. It was observed during the use of pyrene, an insoluble molecular probe in water, a modification of its fluorescent profile in the presence of EPS in comparison to the pluronic P85 (a tri-block copolymer known to form micelles in solution) profile in the same conditions. The temperature of formation is from room temperature to 37° C. The micelles formed rapidly and were left undisturbed for a period of 16 to 24 hours to allow equilibration before fluorescence reading. The estimated critical micellar concentration (0.007% (w/v)) and the presence of a significant excimer peak show that EPS is a potential high loading drug carrier, since the excimer state is attributable to molecular stacking of pyrene in an enclosed environment. An electronic microscopy analysis has been processed on EPS samples, showing semi-spherical structures resembling monolayer liposomes. EPS represents an easy-to-produce, at a reasonable cost, biodegradable polymer that is naturally derived from lactic acid bacteria (LAB) which are food-grade microorganisms with the GRAS status (Generally Recognized As Safe) (see FIGS. 2 and 3). It is understood herein that any bacteria capable of producing a polymer is enclosed in the definition of a bacteria suitable to produce the EPS of the present invention. It is also understood that one having ordinary skills in the art would know what bacteria are suitable for pharmaceutical applications as described in the present application.

The micellar delivery system of the present invention is able to incorporate much higher concentrations of pyrene as compared to P85 (see Example 6) that will later be released slowly over time. This prevents at least some of the damaging effects that high doses induce.

The results obtained by the use of the exopolysaccharide micellar system of the present invention reveal that EPS is an effective delivery vehicle for the delivery of various active molecules including lipophilic drugs. The small size and high in vitro stability of the micelles render them useful for a wide variety of biomedical applications. Their loading capacity for the very hydrophobic pyrene compound shows that it allows incorporation of several different compounds with a high degree of hydrophobicity.

The degree of non-covalent incorporation of physical entrapment of a hydrophobic drug into a micelle is determined by the partition coefficient of the drug between the micellar core and the surrounding aqueous medium. The affinity of the exopolysaccharide micelles for lipophilic compounds was assayed by the determination of the partitioning coefficient (solubilization) for the hydrophobic model compound, pyrene, between the exopolysaccharide micelles and water. This method has been previously used to determine the partitioning coefficient of pyrene between several polymeric formulations forming micelles and water and the critical micellar concentration (CMC). This fluorescence method is based on pyrene's sensitivity to the hydrophobicity of its microenvironment. This is reflected in changes in the ratio of the $I_3/I_1$ bands of its emission spectrum (see FIG. 1). The method requires the measurement of the $I_3/I_1$ ratio for pyrene in micelle solutions of various solvent mixtures. The CMC is calculated by plotting either the $I_3/I_1$(aqueous) peak fluorescence values over the concentrations of polymers or exopolysaccharide. The ratio is at first a measurement of the polarity of the solvent. This plot has a S-shape and the inflection point corresponds to the CMC. Furthermore, by plotting $I_3$ (test solution) on $I_3/I_1$(aqueous) for a range of concentration gives an idea of the capacity to solubilize the pyrene (partitioning coefficient). Finally, $I_4$ or $I_e$ which corresponds to the peak of excimer (pile up of ground state and excited pyrene molecules) represents an accumulation of pyrene in an hydrophobic microdomain. By plotting $I_4$ or $I_e$ (test solution) on $I_4$ or $I_e$ (aqueous or control) for a range of concentration gives an indication about the magnitude of pyrene accumulation in hydrophobic pocket like micelles or micellar like structure. Also, the ratio $I_4$ or $I_e$ (test solution) on $I_3$ (test solution) represents the degree of friction in the hydrophobic domains. A high ratio is a sign of high viscosity.

The in vitro toxicity of the exopolysaccharide micelles was tested by incubating the micelles with a wide range of cell lines for 4-hour, 8-hour, 72-hour and 96-hour periods. The XTT™ or Alamar Blue™ assays were used to quantify the survival rates in the presence of the exopolysaccharide micelles. The capability of the exopolysaccharide to deliver an active molecule was first tested in vitro using 5-Fluorouracil (5-Fu) as a model active molecule. The 4-hour and 8-hour exposure time were removed from the analysis due to the absence of reaction, 5-Fu being a low action drug and EPS showing no toxicities at those times. The 5-Fu/exopolysaccharide formulation was incubated with either B16F10 (murine skin melanoma), Caco-2 (human colon adenocarcinoma) or IEC-6 (rat epithelial small intestine) cells over 72-hour to 96-hour. Vital dyes (XTT or Alamar Blue) were added to supernatants for a period of 4 hours. Absorbance values were collected and plotted to evaluate the survival rate of the cells to the treatment. The results from XTT or Alamar Blue survival assays (Example 6) show a synergy between the EPS and the drug. It is also shown that combined use of 5-Fu and EPS has a higher cytotoxicity than the use of 5-Fu or EPS alone.

Beside the enhancement of in vitro toxicity of a drug which shows a synergy, EPS were used to formulate various molecules like fluorescin, rhodamine, 5-Fu, paclitaxel to demonstrate that EPS change the pharmacokinetic of those molecules (see Example 8) and cause an improvement of absorption, reduction of elimination, increase Cmax, and higher AUCs which leads to better therapeutic efficacy of 5-FU and paclitaxel (see Examples 9 and 10). A better efficacy translate into better overall survival or delay of death.

The exopolysaccharides are easy to use since there is no need for micelle preparation. The exopolysaccharides were dissolved in PBS pH 7.2 and incubated overnight at room temperature, which led to the spontaneous formation of the EPS micellar structure. Micellization process with exopolysaccharide is different than the conventional preparation of micelles (like P85) which is achieved by the addition of water in a dropwise fashion to a solution to form a micelle solution and the micelle solution did not need to be stirred overnight and then dialyzed against milli-Q™ distilled water using dialysis tubing with a change of water every hour for the first four hours and then every three hours for the next twelve hours like it is usually done.

The present invention describes the formation of micelles of different size composed of exopolysaccharide, preferably ranging from 50 to 700 nm. The exopolysaccharide can be isolated from, but not limited to, *Lactobacillus* strain R2C2, *Lactobacillus* strain Inix, *Lactobacillus* strain Es1, *Lactobacillus* strain K2.

The exopolysaccharide not only can form micelles but can act as a biological response modifying agent on cells. As shown in Example 8, exopolysaccharide can activate genes in keratinocytes which shows that exopolysaccharides can be used not only as a drug delivery system but may have a synergistic effect with various drugs.

Example 1

Extraction of EPS

EPS are extracted from biomass of a consortium of bacteria and yeast strains that include without limitation to the following ones: *Lactobacillus* strain R2C2, *Lactobacillus* strain Inix, *Lactobacillus* strain Es1, *Lactobacillus* strain K2, *Candida kefyr*, *Candida norvegensis*. EPS can also be produced from the purified bacterial strain mentioned above.

Example 2

Crude Preparation and Production of EPS

Biomass (either consortium or purified bacterial stain) is added to hot water (0.5 to 5% (w/v)). The temperature of the solution is brought to 95° C. and agitation is applied for a dissolution time of 3 hours. Dissolution of biomass is visually monitored and when no further dissolution occurs the incubation is pursued for an extra hour. A primary filtration is performed to remove aggregates and debris and the filtrate centrifuged. For large volumes (10 L and over) a primary tangential filtration (0.45 µM) is performed to remove aggregates and debris. Filtrate is than concentrated by tangential filtration (3 kDaltons) to a minimal volume. Retentate is centrifuged at 7500 g for 15 minutes to remove the precipitate. An equal volume of ice cold ethanol 100% (−70) is added to the supernatant to precipitate the exopolysaccharides for 1.6 h. After centrifugation 7500 g, 4° C. for 15 minutes, the supernatant is discarded and the pellet resuspended in a minimal volume of water. Solution is centrifuged at 7500 g for 15 minutes. The supernatant containing EPS is freeze-dried to yield the pure EPS.

Example 3

Purified Preparation of EPS

Biomass (either consortium or purified bacterial strain) is added to hot water (0.5 to 5% (w/v)). The temperature of the solution is brought to 95° C. and agitation is applied for a dissolution time of 3 hours. Dissolution of biomass is visually monitored and when no further dissolution occurs the incubation is pursued for an extra hour. A primary filtration is performed to remove aggregates and debris. For large volumes (10 L and over) a primary tangential filtration (0.45 µM) is performed to remove aggregates and debris. Filtrate is concentrated by tangential filtration (3 kDaltons) to a minimal volume. Retentate is centrifuged at 7500 g for 15 minutes to remove the precipitate. An equal volume of ice cold ethanol 100% (−70) is added to the supernatant to precipitate the exopolysaccharides for 16 h. After centrifugation 7500 g, 4° C. for 15 minutes, the supernatant is discarded and the pellet resuspended in a minimal volume of water. Solution is centrifuged at 7500 g for 15 minutes. The supernatant containing EPS is freeze-dried to yield the pure EPS.

Example 4

Fractionation of EPS

Pure EPS are solubilized in water and fractionated by serial passages on membrane of different molecular weight cutoff. As example, when the membranes used are of 100 000, 50 000, 10 000 and 3 000 kDa, it yield fraction of EPS with the following range of molecular weight: EPS>100 000 kDa, 50 000 kDA <EPS>100 000 kDa, 10 000 kDa <EPS>50 000 kDa, 3 000 kDa<EPS>10 000 kDa, EPS<3 000 kDa.

Example 5

Measurement of Critical Micelle Concentration (CMC) of EPS Using Pyrene

A 1% solution of EPS (w/v) in PBS was prepared. The solution was vortexed for 2 minutes until EPS is well resuspended. Multiple dilutions were performed to obtain 2 ml of 0.1%, 0.01%, 0.001% EPS solution. In parallel, a series of borosilicate tubes were prepared to which 20 µl of a pyrene solution (50 µM solubilized in acetone (Sigma Aldrich cat. No. 18-551-5)) were added. The solutions were allowed to dry prior to the addition of the various EPS solutions. Once dried, 2 ml of the EPS solutions were transferred into the borosilicate tubes to be tested. This is called a redissolution test or solubilization or partitioning between water and test conditions. The control tube (containing PBS only) was placed in the cell holder set at 37° C. of an Varian Eclipse™ fluorometer set at Excitation: 340 nm, Emission: 350-600 nm. Samples were incubated over time and read to obtain the partitioning coefficient and CMC measurement. CMC is calculated according to the standard protocols as described previously. The data of Table 1 show the ratio of fluorescence intensity of peak $I_3$ over intensity of peak $I_3$ from PBS solution as a function of the concentration of EPS and P85. This data show that the EPS can solubilize the insoluble probe (pyrene) as much if not more than P85 from the range 0.001% to 0.1%. At higher concentration (1%), P85 seems to keep forming conventional micelles while the EPS start to decline which is explained by a shift in the spectrum profile. This shift is indicative of excimers formation.

TABLE 1

Ratio of fluorescence intensity of peak $I_3$ over intensity of peak $I_3$ from PBS solution in function of the concentration of EPS and P85

| Concentration | P85 | EPS lot 2 |
|---|---|---|
| 0.001% | 1.107 | 1.125 |
| 0.01% | 1.168 | 1.690 |
| 0.1% | 2.564 | 3.989 |
| 1% | 8.813 | 3.476 |

The data of Table 2 show the ratio of fluorescence intensity of peak $I_e$ over intensity of peak $I_e$ from PBS solution in function of the concentration of EPS and P85. This data show that EPS triggers a higher formation of excimer than P85.

TABLE 2

Ratio of fluorescence intensity of peak Ie over intensity of peak Ie from PBS solution in function of the concentration of EPS and P85

| Concentration | P85 | EPS lot 2 |
|---|---|---|
| 0.001% | 0.9619 | 2.241 |
| 0.01% | 1.233 | 19.51 |
| 0.1% | 2.443 | 60.31 |
| 1% | 4.829 | 11.97 |

The data of Table 3 show the ratio of fluorescence intensity of peak $I_e$ over intensity of peak $I_m$ as a function of the concentration of EPS and P85. This data show that the EPS are more viscous than P85.

TABLE 3

Ratio of fluorescence intensity of peak $I_e$ over intensity of peak $I_m$ as a function of the concentration of EPS and P85

| Concentration | P85 | EPS lot 2 |
|---|---|---|
| 0.001% | 0.06239 | 0.1430 |
| 0.01% | 0.07580 | 0.8293 |
| 0.1% | 0.06841 | 1.086 |
| 1% | 0.03935 | 0.2472 |

The data of Table 4 show the ratio of fluorescence intensity of peak $I_3$ over intensity of peak $I_1$ in function of the concentration of EPS and P85. This data show that both P85 and EPS are a polar media.

TABLE 4

Ratio of fluorescence intensity of peak $I_3$ over intensity
of peak $I_1$ in function of the concentration of EPS and P85

| Concentration | P85 | EPS lot 2 |
|---|---|---|
| 0.001% | 0.9271 | 0.9119 |
| 0.01% | 0.9226 | 1.031 |
| 0.1% | 0.9538 | 1.257 |
| 1% | 0.9892 | 1.328 |

Example 6

Formulation of 5 FU with EPS and Studies on B16, IEC-6 and Caco-2 Cells

Caco-2, IEC-6 and melanocytes B16 cells were cultured in DMEM supplemented with 10% FBS. The cells were seeded at $2\times10^3$ cells per well in a 96-well plate and left to rest 24 hours before EPS exposure at various concentrations and also with or without 5 FU (0.001 μg/ml to 10 μg/ml). The cells were grown in a $CO_2$ incubator for 4 extra days. Cell survival was assessed with XTT™ according to manufacturers recommendation. The data obtained show a synergistic effect between 5 FU and the EPS while EPS show no or only modest toxicity. Furthermore, on differentiated Caco-2 cells, EPS from consortium show no toxicity neither alone nor in formulation unlike on proliferative Caco-2 cells where the synergy of EPS is evident. The data are as follows:

TABLE 5

Survival of IEC-6 rat normal small intestine epithelial
cells in presence of different concentrations of
5-fluorouracil and exopolysaccharides

| μg/ml | 5-Fu alone | EPS 1% + 5-Fu | EPS 0.1% + 5-Fu | EPA 0.01% + 5-FU |
|---|---|---|---|---|
| 0 | 100.1 ± 5.2 | 64.2 ± 14.8 | 86.0 ± 4.3 | 97.0 ± 11.1 |
| 5 | 16.9 ± 6.4 | 0.0 ± 2.1 | 0.0 ± 4.8 | 5.4 ± 1.5 |
| 50 | 28.0 ± 4.6 | 7.1 ± 3.5 | 9.3 ± 6.3 | 8.1 ± 5.1 |
| 250 | 35.4 ± 8.2 | 0.4 ± 3.1 | 18.2 ± 6.5 | 37.2 ± 11.7 |
| 500 | 33.4 ± 3.5 | 0.0 ± 5.3 | 22.1 ± 4.1 | 8.3 ± 4.6 |

Table 5 illustrates the results of three days exposure treatments run in quadruplicate and cell survival was revealed by absorbance using the vital dye Alamar Blue™ (Medicorp, Mtl). [NB073]. Percentages of EPS are expressed in (w/v).

TABLE 6

Survival of IEC-6 rat normal small intestine epithelial
cells in presence of different concentrations of
5-Fluorouracil and exopolysaccharides

| μg/ml | 5-Fu alone | EPS 1% + 5-Fu | EPS 0.1% + 5-Fu | EPA 0.01% + 5-FU |
|---|---|---|---|---|
| 0 | 100.0 ± 1.9 | 0.0 ± 6.7 | 91.8 ± 2.3 | 91.3 ± 2.1 |
| 1 | 78.0 ± 3.0 | 0.0 ± 4.3 | 76.7 ± 0.3 | 84.9 ± 1.5 |
| 10 | 75.4 ± 2.9 | 0.0 ± 4.7 | 76.4 ± 0.6 | 83.2 ± 3.1 |
| 50 | 81.8 ± 2.1 | 0.0 ± 4.4 | 71.7 ± 1.1 | 80.6 ± 2.2 |
| 100 | 80.2 ± 0.9 | 0.0 ± 1.2 | 67.0 ± 1.8 | 66.8 ± 2.7 |

Table 6 illustrates the results of three days exposure treatments run in quadruplicate and cell survival was revealed by absorbance using the vital dye Alamar Blue™ (Medicorp, Mtl). [NB073]. Percentages of EPS are expressed in (w/v).

TABLE 7

Survival of Caco-2 human colon adenocarcinoma cells
in proliferation in presence of different concentrations
of 5-Fluorouracil and exopolysaccharides

| μg/ml | 5-Fu alone | EPS 0.1% + 5-Fu (consortium) | EPS 0.1% + 5-Fu (pure strain) |
|---|---|---|---|
| 0 | 100.0 ± 1.2 | 98.0 ± 1.1 | 101.8 ± 2.3 |
| 1 | 74.1 ± 1.9 | 60.5 ± 3.4 | 119.7 ± 4.7 |
| 10 | 78.6 ± 2.4 | 34.2 ± 0.8 | 36.3 ± 0.5 |
| 50 | 80.3 ± 1.8 | 46.4 ± 1.4 | 52.2 ± 1.3 |
| 100 | 52.6 ± 4.8 | 47.4 ± 1.2 | 41.0 ± 1.1 |

Table 7 illustrates the results of four days exposure treatments were run is octoplicate and cell survival was revealed by absorbance using the vital dye XTT™ (Sigma, St-Louis) [NB050]. Percentages of EPS are expressed in (w/v).

TABLE 8

Survival of Caco-2 human colon adenocarcinoma cells
differentiated in presence of different concentrations
of 5-Fluorouracil and exopolysaccharides

| μg/ml | 5-Fu alone | EPS 0.1% + 5-Fu (consortium) | EPS 0.1% + 5-Fu (pure strain) |
|---|---|---|---|
| 0 | 100.0 ± 4.0 | 97.8 ± 1.9 | 105.7 ± 4.2 |
| 1 | 105.7 ± 4.2 | 100.9 ± 5.1 | 69.2 ± 0.3 |
| 10 | 85.6 ± 8.8 | 108.7 ± 4.4 | 75.4 ± 5.2 |
| 50 | 99.6 ± 6.8 | 98.3 ± 6.0 | 71.9 ± 2.8 |
| 100 | 78.1 ± 0.7 | 88.2 ± 3.6 | 77.2 ± 1.6 |

Table 8 illustrates the results of four days exposure treatments were run is octoplicate and cell survival was revealed by absorbance using the vital dye XTT™ (Sigma, St-Louis) [NB050]. Percentages of EPS are expressed in (w/v).

TABLE 9

Survival of B16F10 murine skin melanoma cells in presence of different
concentrations of 5-Fluorouracil and expolysaccharides

| μg/ml | 5-Fu alone | EPS 0.1% + 5-Fu (consortium) | EPS 0.1% + 5-Fu (pure strain) |
|---|---|---|---|
| 0 | 100.0 ± 4.1 | 95.8 ± 9.6 | 56.4 ± 4.5 |
| 1 | 62.6 ± 6.6 | 20.5 ± 1.4 | 21.2 ± 1.4 |
| 10 | 65.4 ± 10.4 | 35.4 ± 10.7 | 26.4 ± 3.4 |
| 50 | 54.9 ± 8.9 | 18.7 ± 2.7 | 28.2 ± 4.9 |
| 100 | 38.8 ± 8.5 | 20.9 ± 6.5 | 26.8 ± 2.6 |

Table 9 illustrates the results of four days exposure treatments were run is octoplicate and cell survival was revealed by absorbance using the vital dye XTT™ (Sigma, St-Louis) [NB050]. Percentages of EPS are expressed in (w/v).

Example 7

Biological effects of EPS on Keratinocytes

HEKa (human epithelial keratinocytes, adult, Cascade Biologics), grown in Medium 154 supplemented with human keraticocyte growth supplement (HKGS), were exposed to exopolysaccharide (10 μg/ml) and the RNA extracted using Rneasy purification columns (Qiagen) as per manufacturers specifications. The RNA samples from control and treated cells was labeled with Cy3 and Cy5 respectively, and applied to human 1.7 K microarray (Microarray Centre, University Health Network, Toronto) for competitive hybridization. Exopolysaccharides regulate the expression of a variety of genes that may be advantageous for cosmeceutical purposes but also shows that they are not inert and modulate genes that indicate the type of drugs that be formulated with EPS.

TABLE 10

Genes regulated by Exopolysaccharides

| Down regulated genes | Up regulated genes |
|---|---|
| Tumor necrosis factor (TNF) | TGF-beta induced (TGFBi) |
| Cyclooxygenase 2 (COX) | Transglutaminase 2 (Tgase 2) |
| | Transgelin (TAGLN2) |
| | Thrombospondin 1 (THBS1) |
| | Keratin 7 (KRT7) |
| | Ferritin light polypeptide (FTL) |

Example 8

Change of Pharmacokinetic of Markers with EPS

Fluorescein (FL) pharmacolinetic on unfasten Wistar female rats of 200 g and 8 weeks of age. Fluorescein concentration is 1 mg/kg. Exopolysaccharides (EPS) are diluted in water at 1% and 5% (w/v). Fluorescein is added to the latter solutions and vortexed. Formulations are fed to the animals with a canula. 200 µl blood samples are collected through the jugular vein every 30 minutes for 2.5 hours. A final bleeding is made at 3.5 h. Plasma are collected immediately after centrifugation (10 min @ 1300 g). Plasma are frozen on dry ice until further analysis: 50 µl of plasma are diluted in 550 µl of saline 0.7% (w/v) and analyzed with a Varian Eclipse Spectrofluorometer (Excitation: 495 nm Emission: 515 nm). Concentrations were determined on a fluorescein standard curve (FL diluted in saline 0.7% and 50 µl of normal serum as in the sample analysis).

TABLE 11

Fluorescein concentrations over time

| Time (h) | FL-Water | Std Err | FL-EPS 1% | Std Err | FL-EPS 5% | Std Err |
|---|---|---|---|---|---|---|
| 0.0 | 37.10 | 3.55 | 54.79 | 15.40 | 36.77 | 3.38 |
| 0.5 | 218.30 | 49.40 | 298.26 | 24.61 | 360.46 | 62.08 |
| 1.0 | 145.95 | 19.92 | 319.20 | 166.54 | 151.50 | 62.78 |
| 1.5 | 75.25 | 19.83 | 140.76 | 68.07 | 136.04 | 38.69 |
| 2.0 | 74.48 | 17.46 | 73.09 | 21.14 | 95.66 | 25.78 |
| 2.5 | 71.74 | 14.57 | 48.31 | 10.39 | 92.44 | 22.45 |
| 3.5 | 54.63 | 10.28 | 70.60 | 31.08 | 88.47 | 26.78 |

EPS used at 1% and 5% show a better absorption than non formulated fluorescein. Higher Cmax were obtained for both concentration around 1 h after the gastric intubation. Overall, EPS 5% show a better absorption of the drug up to 3.5 h. The result of a better absorption is superior AUC for both concentration of EPS this translating to a better drug exposure and thus better treatments (see Example 10).

Example 9

Formulation of B16 Tumors in Muscle following i.m. Injection of B16 Cells Treated with a Formulation of Paclitaxel Fifteen mice in group P1 (100× stock=100 mM or 85.3 mg/ml, prepared from powdered stock in DMSO) and fourteen mice in group P2 (10× stock=10 mM in 1% EPS (in PBS), or 8.5 mg/ml, prepared from 100 µl P1 in 900 µl 1% EPS (in PBSP)). Cells (50000 cells per 50 µl injections) for a concentration of $10^6$ cells per ml. The remaining of the test was performed as follows:

Cells from $1XT_{75}$ (80% confluence) are trypsinized with 2 ml trypsin, diluted in 12 ml media, spun down, rinsed once in 5 ml PBS, and resuspended in 2 ml PBS. Cells are then counted and concentration adjusted to $10^6$ cells per ml.

P1 treatment: Add 200 µl P1 stock and 180 µl PBS of cell suspension ($10^6$ cells) and incubate at room temperature 3 hrs. Final Paclitaxel=1 mM, DMSO=1%.

P2 treatment: Add 200 µl P2 stock to 1.8 ml of cell suspension ($10^6$ cells) and incubate at room temperature 3 hrs. Final Paclitaxel=0.1 mM, DMSO=1%, EPS=0.1%.

1 ml of cells from P1 and P2 treatment groups were replated following a rinse in PBS. No growth was observed from either group after 2 weeks in culture.

TABLE 12

Tumor-free mice (%)

| | Formulation | |
|---|---|---|
| | P1 | P2 |
| Growth in tissue culture | negative | negative |
| Intramuscular tumor formation | 12/15 | 1/14 |

Cells treated with Paclitaxel do not have the capacity to recover from this treatment in tissue culture, however, in an environment rich in nutrients and growth factors, such as in vivo within the muscle, the cells can recover from the drug and form intramuscular tumors. However, as shown herein, the presence of EPS potentiates the effect of Paclitaxel in this model.

Example 10

Treatment with a 5 FU/EPS Formulation of Mice Grafted with B16 cells Injected i.p.

Tumor cells were trypsinized and washed 3 times with PBS. Cells (1×10E6) were injected i.p. to Balb/c mice to induce a cancer in the peritoneal cavity. After 4 days of implantation, treatments of 5 FU alone (100 mg/kg) or EPS alone (0.1% w/v) or a combination of both were given to the mice. Survival was observed for 44 days from day 0 of injection. An additive effect was observed, between EPS and 5 FU from day 29 leading to a better survival than the group treated with 5 FU alone. EPS alone show efficacy until day 29 compared with other treatments but protects the animals better overall. This highlighting again that EPS are not inert and may contribute to the therapeutic index.

TABLE 13

Tumor-free mice over time (%)

| Days | Saline (Placebo) | 5-FU | EPS 0.1% (w/v) | EPS 0.1% (w/v) + 5-FU |
|---|---|---|---|---|
| 0 | 100 | 100 | 100 | 100 |
| 15 | 12.5 | 62.5 | 37.5 | 62.5 |
| 29 | 12.5 | 12.5 | 37.5 | 37.5 |
| 44 | 12.5 | 12.5 | 37.5 | 25 |

Example 11

Modification of the Pharmacokinetic of Rhodamine Formulated with EPS

The pharmacokinetic of Rhodamine 123 (R123) was performed on unfasten Wistar female rats of 200 g and 8 weeks of age. Rhodamine concentration is 5 mg/kg. Exopolysaccharides (EPS) were diluted in water at 1% and 3% (w/v). Rhodamine is added to the latter solutions and vortexed. Formulations are fed to the animals with a canula and 200 µl blood samples are collected through the jugular vein every hour for 4 hours (plus 1 sample at 0.5 h). Plasma are collected immediately after centrifugation (10 min @ 13000 g). Plasma are frozen on dry ice until further analysis: 50 µl of plasma are diluted in 550 µl of saline 0.7% (w/v) and analyzed with a Varian Eclipse™ Spectrofluorometer (Excitation: 505 nm Emission: 540 nm). Concentrations were determined on a Rhodamine 123 standard curve (R123 diluted in saline 0.7% and 50 µl of normal serum as in the sample analysis). The data are as follows:

TABLE 14

Rhodamine 123's concentration over time

| Time (h) | R123 - Water (ng/ml) | R123 - EPS 1% (ng/ml) | R123 - EPS 3% (ng/ml) |
|---|---|---|---|
| 0.0 | 2.2 ± 2.2 | 0.2 ± 0.1 | 1.3 ± 0.7 |
| 0.5 | 20.4 ± 2.2 | 10.1 ± 2.2 | 21.7 ± 4.2 |
| 1.0 | 20.9 ± 2.6 | 11.6 ± 3.0 | 24.3 ± 3.5 |
| 2.0 | 15.4 ± 2.0 | 9.1 ± 2.9 | 20.2 ± 4.8 |
| 3.0 | 10.9 ± 1.4 | 6.0 ± 1.2 | 20.3 ± 4.6 |
| 4.0 | 11.2 ± 1.8 | 3.0 ± 0.7 | 15.7 ± 3.6 |

Rhodamine formulated with EPS used at 3% show approximately the same absorption as in water except that the AUC (area under the curve) is increased. Absorption, distribution and elimination seem to be closely linked between those two groups showing no influence of the EPS in the blood circulation. EPS 1%, on their side, show a peculiar profile. The absorption is slower and lower. EPS 1% might retain the R123, preventing it from penetrating in the blood stream or EPS 1% could stay with R123 and block its fluorescence.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A delivery composition for delivery of an active molecule to a patient, said delivery system comprising a population of exopolysaccharide micelles comprising exopolysaccharide produced by a bacterium selected from the group of bacteria consisting of *Lactobacillus* strain R2C2 (IDAC 041202-3), *Lactobacillus* strain Inix(IDAC 041202-4), *Lactobacillus* strain Esl (IDAC 041202-2), *Lactobacillus* strain K2 (IDAC 041202-1), each said micelle including a core for containing said active molecule.

2. The delivery composition of claim 1, wherein said active molecule is selected from the group consisting of DNA, RNA, protein, peptide, peptidomimetic, virus, bacteria, nutriceutical product and pharmaceutical agent.

3. The delivery composition of claim 2, wherein said pharmaceutical agent is selected from the group consisting of analgesic, anesthetic, antibiotic, anticancer, anti-inflammatory, and antiviral.

4. The delivery composition of claim 3, wherein said anticancer agent is selected from the group consisting of alkylating agents, alkyl sulfonates, aziridines, ethylenimines, methylamelamines, acetogenins, camptothecin, bryostatin, callystatin, CC-1065, cryptophycins, dolastatin, duocarmycin, eleutherobin, pancratistatin, sarcodictyin, spongistatin, nitrogen mustards, nitrosureas, antibiotics, anti-metabolites, folic acid analogues, denopterin, methotrexate, pteropterin, trimetrexate, purine analogs, pyrimidine analogs, androgens, anti-adrenals, folic acid replenisher, aceglatone, aldophosphamide glycoside, aminolevulinic acid, amsacrine, bestrabucil, bisantrene, edatraxate, defofamine, demecolcine, diaziquone, elformithine, elliptinium acetate, epothilone, etoglucid, gallium nitrate, hydroxyurea, lentinan, lonidamine, maytansinoids, mitoguazone, mitoxantrone, mopidamol, nitracrine, pentostatin, phenamet, pirarubicin, podophyllinic acid, 2-ethylhydrazide, procarbazine, PSK, RTM, razoxane, rhizoxin, sizofuran, spirogermanium, tenuazonic acid, triaziquone, 2,2',2"-trichlorotriethylamine, trichothecenes, urethan, vindesine, dacarbazine, mannomustine, mitobronitol, mitolactol, mitolactol, pipobroman, gacytosine, arabinoside, thiotepa, taxanes, chlorambucil, gemcitabine, 6-thioguanine, mercaptopurine, methotrexate, platinum, vinblastine, platinum, etoposide, ifosfamide, mitomycin C, mitoxantrone, vincristine, vinorelbine, navelbin, novantrone, teniposide, daunomycin, aminopterin, xeloda, ibandronate, CPT-11, topoisomerase inhibitor RFS 2000, difluoromethylornithine, retinoic acid, capecitabine, and anti-hormonal agents that act to regulate or inhibiting hormone action in hormonal dependent cancers.

5. The delivery composition of claim 4, wherein said antihormonal agent is an anti-estrogens or an anti-androgens selected from the group consisting of flutamide, nilutamide, bicalutamide, leuprolide, and goserelin, and pharmaceutically acceptable salts, acids or derivatives thereof.

6. The delivery composition of claim 4, wherein said alkylating agents is selected from the group consisting of thiotepa and cyclosphosphamide(CYTOXAN).

7. The delivery composition of claim 4, wherein said alkyl sulfonates is selected from the group consisting of busulfan, improsulfan and piposulfan.

8. The delivery composition of claim 4, wherein said aziridines is selected from the group consisting of benzodopa, carboquone, meturedopa, and uredopa.

9. The delivery composition of claim 4, wherein said methylamelamines is selected from the group consisting of altretamine, triethylenemelamine, triethylenethiophosphaoramide and trimethylolomelamine.

10. The delivery composition of claim 4, wherein said acetogenins is selected from the group consisting of bullatacin and bullatacinone.

11. The delivery composition of claim 4, wherein said camptothecin is the synthetic analogue topotecan.

12. The delivery composition of claim 4, wherein said CC-1065 is selected from the group consisting of adozelesin carzelesin and bizelesin synthetic analogues thereof.

13. The delivery composition of claim 4, wherein said cryptophycins is selected from the group consisting of cryptophycin 1 and cryptophycin 8.

14. The delivery composition of claim 4, wherein said duocarmycin is selected from the group consisting of KW-2189 and CBI-TMI.

15. The delivery composition of claim 4, wherein said nitrogen mustards is selected from the group consisting of chlorambucil, chlornaphazine, cholophosphamide, estramustine, ifosfamide, mechlorethamine, mechlorethamine oxide hydrochloride, melphalan, novembichin, phenesterine, prednimustine, trofosfamide and uracil mustard.

16. The delivery composition of claim 4, wherein said nitrosureas is selected from the group consisting of carmustine, chlorozotocin, fotemustine, lomustine, nimustine, ranimustine.

17. The delivery composition of claim 4, wherein said anti-metabolites is selected from methotrexate and 5-fluorouracil (5-FU).

18. The delivery composition of claim 4, wherein said purine analogs is selected from the group consisting of fludarabine, 6-mercaptopurine, thiamiprine and thioguanine.

19. The delivery composition of claim 4, wherein said pyrimidine analogs is selected from the group consisting of ancitabine, azacitidine, 6-azauridine, carmofur, cytarabine, dideoxyuridine, doxifluridine, enocitabine and floxuridine.

20. The delivery composition of claim 4, wherein said androgens is selected from the group consisting of calusterone, dromostanolone propionate, epitiostanol, mepitiostane, testolactone.

21. The delivery composition of claim 4, wherein said anti-adrenals is selected from the group consisting of aminoglutethimide, mitotane and trilostane.

22. The delivery composition of claim 4, wherein said anticancer agent is a taxane.

23. The delivery composition of claim 3, wherein said antibiotics is selected from the group consisting of enediyne antibiotics, aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin, deoxydoxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin.

24. The delivery composition of claim 23, wherein said enediyne antibiotics is selected from the group consisting of calicheamicin, dynemicin, esperamicin, neocarzinostatin chromophore and related chromoprotein enediyne antibiotic chromomophores.

25. The delivery composition of claim 24, wherein said calicheamicin is selected from the group consisting of calicheamicin $_{\gamma l}1$ and calicheamicin $O_{11}$.

26. The delivery composition of claim 24, wherein said dynemicin is dynemicin A.

27. The delivery composition of claim 1, wherein said micelles have a diameter varying from about 50 nanometers to about 700 nanometers.

28. A pharmaceutical composition comprising the delivery composition of claim 1 in association with a pharmaceutically acceptable carrier.

29. An immunomodulator composition comprising the delivery system of claim 1 in association with a pharmaceutically acceptable carrier.

30. A method for delivering an active molecule to a patient comprising the step of administering the composition of claim 28 to said patient.

31. The method of claim 30, wherein said administering can be by a route selected from the group consisting of local, parenteral, peritoneal, mucosal, dermal, epidermal, subcutaneous, transdermal, intramuscular, nasal, oral, topical, vaginal, rectal, intra-ocular, intravenous, intra-arterial and by inhalation.

32. A method for producing the delivery composition of claim 1, comprising the step of incubating exopolysaccharide in a suitable medium for a time sufficient to form a micelle.

* * * * *